United States Patent [19]

Rebsdat et al.

[11] 4,349,417
[45] Sep. 14, 1982

[54] PROCESS FOR THE MANUFACTURE OF EXTREMELY PURE MONOETHYLENE GLYCOL

[75] Inventors: Siegfried Rebsdat, Burg; Sigmund Mayer, Burgkirchen; Josef Alfranseder, Hofschallern; Iwo Schaffelhofer, Burghausen, all of Fed. Rep. of Germany

[73] Assignee: Hoechst Aktiengesellschaft, Fed. Rep. of Germany

[21] Appl. No.: 223,590

[22] Filed: Jan. 9, 1981

[30] Foreign Application Priority Data

Jan. 18, 1980 [DE] Fed. Rep. of Germany ....... 3001727

[51] Int. Cl.³ ............... B01D 3/34; C07C 29/80; C07C 31/20
[52] U.S. Cl. .................. 203/33; 203/36; 203/37; 203/38; 203/71; 568/867; 568/868
[58] Field of Search ............ 203/38, 37, 36, 33, 203/18, 71, 73; 568/867, 868, 871

[56] References Cited

U.S. PATENT DOCUMENTS

| | | | |
|---|---|---|---|
| 2,788,373 | 4/1957 | Mills et al. | 568/871 |
| 2,793,235 | 5/1957 | Jenkinson | 568/871 |
| 3,408,268 | 10/1968 | Pitts et al. | 203/18 |
| 3,875,019 | 4/1975 | Cocuzza et al. | 203/18 |
| 3,904,656 | 9/1975 | Broz | 568/867 |
| 3,970,711 | 7/1976 | Reiche et al. | 568/868 |
| 4,225,394 | 9/1980 | Cox et al. | 203/37 |

FOREIGN PATENT DOCUMENTS 45-10324  4/1970  Japan ..................... 203/37

Primary Examiner—Wilbur L. Bascomb, Jr.
Attorney, Agent, or Firm—Connolly and Hutz

[57] ABSTRACT

Ethylene oxide and water are reacted in a reactor and the reaction product is subjected to distillation in a plurality of distillation columns, in the first columns water and components having a boiling point below that of monoethylene glycol and higher ethylene glycols, if any, being distilled off. To obtain extremely pure monoethylene glycol alkali metal compounds are added at a point between the reactor and the monoethylene glycol distillation column in an amount to adjust the pH of the product entering the latter column to a value of from 7 to 10. The monoethylene glycol obtained in this manner is especially pure and has very low UV absorption values. It is, therefore, especially suitable for the manufacture of polyester fibers.

8 Claims, 1 Drawing Figure

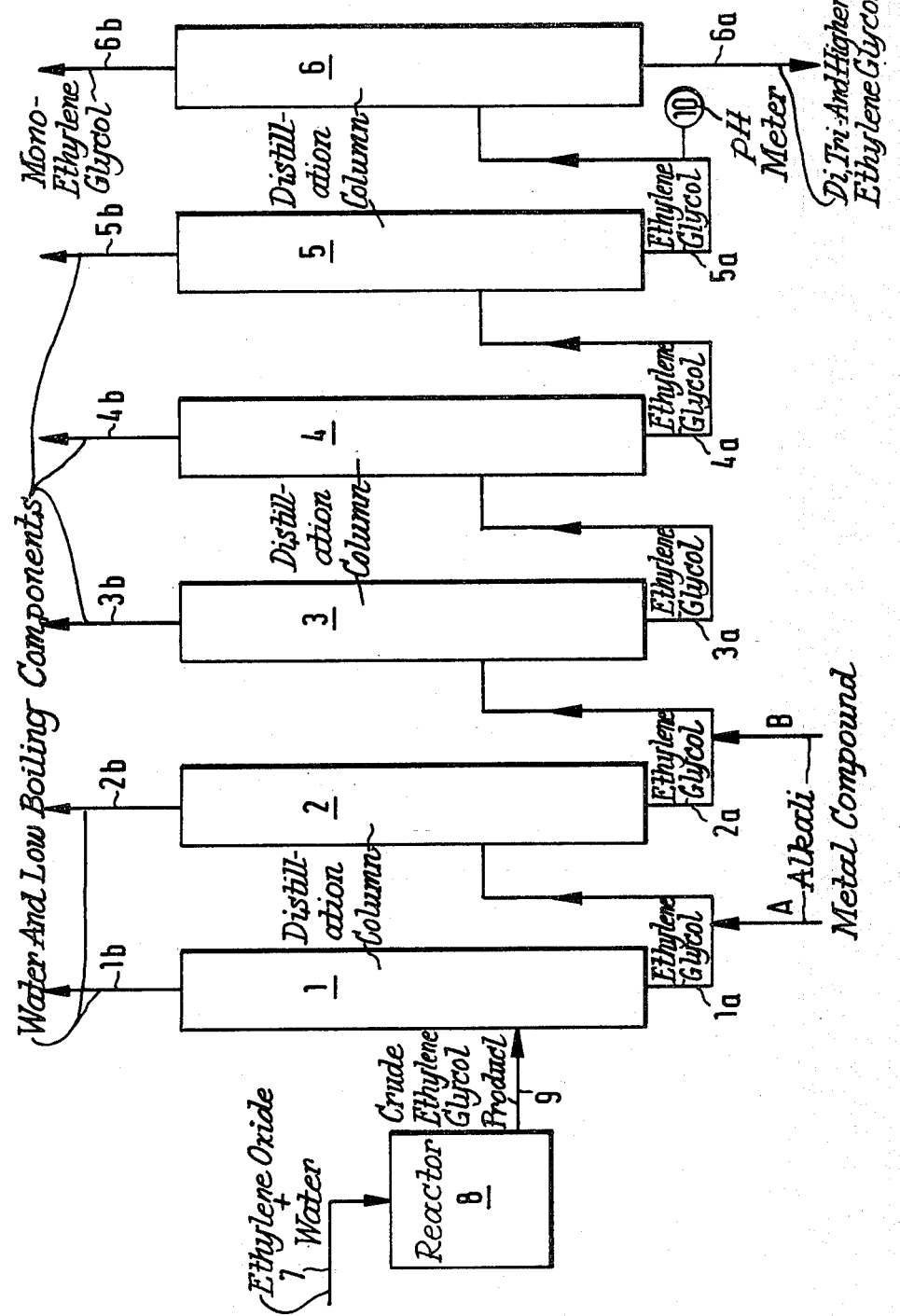

PROCESS FOR THE MANUFACTURE OF EXTREMELY PURE MONOETHYLENE GLYCOL

This invention relates to a process for the manufacture of extremely pure monoethylene glycol, which comprises reacting ethylene oxide and water in a reactor and transferring the reaction product to a distillation zone comprising several distillation columns interconnected by tubes, in which zone at least the two first columns are used to distil off water and the components having a boiling point below that of monoethylene glycol and in the following column monoethylene glycol and higher ethylene glycols, if any, are successively distilled at the head.

It is known to react ethylene oxide, preferably obtained by direct oxidation of ethylene with oxygen and/or air in contact with silver catalysts, with water (in an about 5 to 50-fold molar excess) in a reactor at a temperature of about 160° to 230° C. and under a pressure of about 2 to 6 MPa to give preponderantly monoethylene glycol. This reaction (hydration) is preferably carried out without catalyst and monoethylene glycol is obtained from the reaction product (reaction mixture) by distillation.

For distillative (fractional) working up the reaction product is passed through a distillation zone comprising a plurality of columns, generally 3 to 10 and preferably 3 to 7 columns, interconnected by tubes (cf. Ullmann's Enzyklopädie der technischen Chemie, 4th edition, volume 8, pages 200–203 and, for example, German Offenlegungsschrift No. 2,364,151).

In this known distillative working up of the reaction product, resulting from the reaction of ethylene oxide with water, the excess amount of water and impurities, if any, the boiling points of which are below that of monoethylene glycol (low boiling components), for example formaldehyde, acetaldehyde and the like, are first distilled off in the so-called dehydration stage comprising generally at least 2 columns, preferably 2 to 5 columns. Hence, water and low boiling constituents are removed in stages. Normally, the first column (first dehydration stage) is operated under a pressure of about 0.8 to 2 MPa and at a temperature of about 140° to 180° C. and the following columns are operated under a relatively low pressure or without pressure at about the same or slightly higher temperature (as compared to the first column).

After having distilled off in the dehydration stage water and low boiling components from the reaction product of crude ethylene oxide and water, the product the water content of which is now less than about 0.1% by weight, is transferred to the ethylene glycol distillation stage generally comprising 1 to 3 columns. In the first column monoethylene glycol is withdrawn at the head at a temperature of about 140° to 170° and under a pressure of about 2 to 4 kPa. In the subsequent columns the sump of the monoethylene glycol column can be further fractionated, whereby, for example, diethylene glycol, triethylene glycol and higher ethylene glycols are obtained (cf. loc. cit.).

Monoethylene glycol, which is used for the manufacture of fibers (by condensation of the glycol, for example, with dimethyl terephthalate) should have an extremely high purity.

As a measurement for this purity the transmission value in ultraviolet high of a wave length of 220 nm is determined. It should be above 67%.

Monoethylene glycol manufactured by the aforesaid known process does not have this required purity. On the other hand, this process constitutes an especially favorable mode for the manufacture of relatively pure monoethylene glycol.

Several proposals have been made concerning the manufacture of pure monoethylene glycol.

German Offenlegungsschrift No. 1,668,052 and German Auslegeschrift No. 2,558,039 describe a process for the purification of ethylene glycols wherein the glycols are passed through an ion exchange resin.

It is recommended in German Offenlegungsschrift No. 1,593,120 to carry out the above distillation process for working up the reaction product from ethylene oxide and water in the presence of an antioxidant, in particular an aromatic amine or phenol. German Offenlegungsschrift No. 2,751,383 describes a process for the manufacture of ethylene glycols of high purity and low UV absorption values starting from ethylene oxide, wherein the hydration of the ethylene oxide is carried out by using the water which is obtained from the washing step of the crude ethylene oxide prior to the hydration step and which water contains sodium boron hydride as additive.

These known processes for the manufacture of monoethylene glycol are not satisfactory in that an additional purifying operation (such as the above mentioned ion exchange) is required or that prior to or during the distillation of the reaction product of ethylene oxide and water additives must be added which may contaminate either as such (for example phenol) or in the form of secondary products (for example boric acid esters from boron hydrides) the monoethylene glycol obtained.

It is, therefore, the object of the present invention to improve the aforesaid distillation process for working up the reaction product resulting from the reaction of ethylene oxide and water in such a manner that the indicated disadvantages do no longer occur and that the monoethylene glycol obtained has the required UV purity.

Surprisingly, it has been found that extremely pure monoethylene glycol (i.e. UV pure ethylene glycol) can be obtained by the aforesaid distillation process by carrying out the distillation in the presence of alkali metal compounds in an amount such that the crude monoethylene glycol passing into the monoethylene glycol column has a pH of 7 to 10.

The present invention, therefore, provides a process for the manufacture of extremely pure monoethylene glycol by reacting ethylene oxide and water in a reactor and transferring the reaction product to a distillation zone comprising a plurality of distillation columns interconnected by tubes, at least the first two columns being used for distilling off water and the components having a boiling point below that of monoethylene glycol and in the following columns monoethylene glycol and higher ethylene glycols, if any, being distilled at the head, which comprises adding to the reaction product, behind the reactor and before the column from which the monoethylene glycol is distilled at the head, compounds of alkali metals selected from the group consisting of the alcoholates, hydroxides, oxides and salts of weak acids, in an amount such that on entering the monoethylene glycol column the product has a pH of 7 to 10.

The alkali metal compounds are preferably added behind the first or second distillation column (dehydration stage), that is to say the compounds are added to the product flow (crude monoethylene glycol) preferably in the conduit through which the sump product of the first column is transferred to the second column or the conduit for passing the sump product of the second column into the third column.

Prior to entering the monoethylene glycol column the product (crude monoethylene glycol) preferably has a pH of 7.2 to 8.9, more preferably 7.5 to 8.5.

The pH is suitably measured with a usual pH meter with addition of distilled water. A sample is preferably taken from the conduit passing the product flow from the bottom of the last column of the dehydration stage into the monoethylene glycol column.

According to the invention, alkali metal alcoholates, alkali metal hydroxides, alkali metal oxides and/or alkali metal salts of weak acids are used to adjust the pH, the respective sodium and potassium compounds being preferred. Suitable alcoholates are preferably those with 1 to 3 carbon atoms, for example sodium methylate and sodium ethylate.

Suitable alkali metal salts of weak acids are preferably salts of carbonic acid, for example potassium carbonate, potassium bicarbonate and sodium carbonate.

From among the alkali metal compounds to be used according to the invention carbonates and hydroxides are preferred, in particular sodium hydroxide (NaOH) and potassium hydroxide (KOH).

The amount of alkali metal compound required to adjust the pH of the invention can vary within wide limits. In general, it is in the range of from 0.1 to 500 mg, preferably 1 to 100 mg per kg of ethylene oxide and water used for hydration.

The alkali metal compound is suitably used in the form of an aqueous, alcoholic, aqueous-alcoholic, or aqueous-glycolic solution. In the case of alcohols being used, methanol, ethanol, propanol and/or isopropanol are preferred.

The concentration of the solutions used is not critical. It can vary within wide limits. Normally, 3 to 30% by weight solutions and preferably 15 to 25% by weight solutions are used. The solutions are suitably metered in by a common dosing device which is generally regulated by the pH meter.

The process of the invention yields monoethylene glycol of a surprisingly high purity. The transmission value thereof in UV light of 220 nm is, in general, far above the desired specification value. In addition, the monoethylene glycol prepared in this manner as well as the higher ethylene glycols (which also should have a high purity) are free from foreign compounds. A further important advantage of the process of the invention is that it substantially solves also the problem of aqueous mother liquors containing ethylene glycol, forcibly obtained in the manufacture of ethylene oxide by direct oxidation of ethylene (cf. German Auslegeschrift No. 2,558,039), as it is possible to add a relatively large amount of said mother liquors to the crude monoethylene glycol without the UV purity of the monoethylene glycol obtained therefrom being noticeably reduced.

In the above-described known distillation process corrosion often occurs in the individual distillation columns. As compared therewith, no corrosion can be observed in the distillation columns when operating according to the invention. The addition of alkali metal compounds eliminates said corrosion.

Moreover, the process of the invention is simple, economical and it can be combined with the known distillation and, thus, carried out in existing plants.

The extremely pure monoethylene glycol obtained by the process of the invention is used, in particular, for the manufacture of fibers (polyester fibers).

The invention will now be described in detail with reference to the accompanying drawing representing a simplified flow scheme of the known hydration and distillation process.

Ethylene oxide (crude) and water, fed through conduit 7, are reacted in reactor 8. The reaction product is passed through conduit 9 to columns 1 to 6, interconnected by conduits 1a to 5a. Columns 1 to 5 are the dehydration stages while column 6 is the monoethylene glycol column.

In columns 1 to 5 the low boiling components and water are distilled off from the reaction product and discharged through conduits 1b to 5b. Crude monoethylene glycol entering column 6 through conduit 5a contains less than 0.1% by weight of water. In column 6 the monoethylene glycol is distilled, it is withdrawn through conduit 6b. The sump product of column 6 consists of di-, tri- and higher ethylene glycols. It is discharged through conduit 6a.

The points at which alkali metal compounds are preferably metered in according to the invention to adjust the pH of the crude monoethylene glycol to a value of 7 to 10 are indicated in the drawing by arrows A and B. The pH meter is installed in a branch current of the conduit leading to the monoethylene glycol column. It is characterized by a circle and number 10.

The following examples illustrate the invention.

EXAMPLE 1 (Comparison)

12,000 kg of crude ethylene oxide containing 33% by weight of ethylene oxide, 1% by weight of aldehyde (sum of aldehydes, mainly formaldehyde and acetaldehyde) and 66% by weight of water were mixed with 32,000 kg of water and continuously reacted in a conventional pressure reactor (hydration reactor) at 220° C. and 5 MPa. The reaction product was transferred to the distillation zone comrising 6 columns as shown in the drawing.

In the first column a mixture of water and low boiling impurities was distilled off under a pressure of 1.5 MPa and at a temperature of 178° C. (sump temperature). The sump product of the first column was further dehydrated in the following 4 columns. The second column was operated at 145° C. at atmospheric pressure, the third column at 160° C. and atmospheric pressure, the fourth column at 150° C. and 50 kPa and the fifth column was operated at 155° C. and 25 kPa. The sump product of the fifth column having a water content of less than 0.1% by weight was passed into column 6 (monoethylene glycol column) via conduit 5a. Rectification was performed at 158° C. and 3 kPa.

The transmission of the monoethylene glycol obtained in this manner was tested in a conventional UV measuring device at a wave length of 220 nm. It was found to be 57%.

The sump product of the fifth dehydration stage (column 5) had a pH of 6.3, measured with a conventional pH meter (10) (cf. the drawing) with addition of water.

EXAMPLE 2

The process was carried out as described in Example 1, with the exception that 200 g/hr of NaOH, corresponding to 4.5 mg/hr of NaOH per kilogram of ethylene oxide and water used (total amount 44,000), were introduced through conduit A (cf. the drawing) into conduit 1a in the form of a 20% by weight aqueous solution by means of a usual dosing device. The sump product of the fifth column had a pH of 8.0.

The value of UV transmission at 220 nm of the monoethylene glycol withdrawn at the head of the sixth column was found to be 87%.

EXAMPLE 3

The process was carried out as specified in Example 2 while adding 100 g/hr of NaOH, corresponding to 2.3 mg/hr of NaOH per kilogram of ethylene oxide and water used. The sump product of the fifth column had a pH of 7.6 the UV transmission was found to be 79%.

EXAMPLE 4

The process was carried out as described in Example 2 while adding 300 g/hr of NaOH or 7.0 mg/hr of NaOH per kilogram of ethylene oxide and water used. The sump product of the fifth column had a pH of 8.9. The UV transmission was found to be 82%.

EXAMPLE 5

The process was carried out as described in Example 2 while adding 50 g/hr of NaOH, corresponding to 1.2 mg/hr of NaOH per kilogram of ethylene oxide and water used. The sump product of the fifth column had a pH of 7.2 and the UV transmission was found to be 67%.

EXAMPLE 6

The process was carried out as described in Example 1, with the exception that 2,000 g/hr of NaOH, corresponding to 45.5 mg/hr of NaOH per kilogram of ethylene oxide and water, were introduced into conduit 2a in the form of a 20% by weight aqueous solution by means of a conventional dosing device through conduit B (cf. drawing). The sump product of the fifth column had a pH of 9.5.

The UV transmission at 220 nm of the monoethylene glycol discharged at the head of the sixth column was found to be 73%.

EXAMPLE 7

The process was carried out as described in Example 6 while adding 200 g/hr of NaOH, corresponding to 4.5 mg/hr of NaOH per kilogram of ethylene oxide and water used. The sump product of the fifth column had a pH of 7.8. The UV transmission was found to be 78%.

What is claimed is:

1. In a process for the manufacture of extremely pure monoethylene glycol by reacting ethylene oxide and water in a reactor and transferring the reaction product stream to a distillation zone comprising a plurality of distillation columns interconnected by tubes, at least two distillation columns being used for distilling off water and those components of said reaction product stream having a boiling point below that of monoethylene glycol and at least one distillation column downstream of these first two columns being a glycol distillation column used to distil at its head a reaction product component consisting essentially of monoethylene glycol, the improvement which comprises: adding to the reaction product stream downstream from the reactor and upstream from said glycol distillation column a compound of an alkali metal selected from the group consisting of an alcoholate, a hydroxide, an oxide, a salt of a weak acid, and mixtures thereof, in an amount such that on entering the glycol distillation column the reaction product stream has a pH of 7 to 10.

2. The process as claimed in claim 1, wherein said alkali metal compound is added downstream from the first distillation column in said distillation zone.

3. The process as claimed in claim 2 wherein there are at least three distillation columns upstream of said glycol distillation column, and a said alkali metal compound is added upstream from the third distillation column in said distillation zone.

4. The process as claimed in claim 1, wherein the pH is adjusted to a value of 7.2 to 8.9.

5. The process as claimed in claim 1, wherein the pH is adjusted to a value of 7.5 to 8.5.

6. The process as claimed in claim 1, wherein the compound of an alkali metal is added in the form of a 3 to 30% by weight aqueous solution.

7. The process as claimed in claim 6, wherein the alkali metal compound is selected from the group consisting of a hydroxide, a carbonate, and mixtures thereof.

8. The process as claimed in claim 6, wherein the alkali metal compound is selected from the group consisting of sodium hydroxide, potassium hydroxide, and mixtures thereof.

* * * * *